(12) United States Patent
Horisaka et al.

(10) Patent No.: US 8,197,652 B2
(45) Date of Patent: Jun. 12, 2012

(54) NOX SENSOR

(75) Inventors: Sumiko Horisaka, Nagoya (JP); San Jae Lee, Ama-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 407 days.

(21) Appl. No.: 12/413,866

(22) Filed: Mar. 30, 2009

(65) Prior Publication Data

US 2009/0242401 A1 Oct. 1, 2009

(30) Foreign Application Priority Data

Mar. 31, 2008 (JP) .................. 2008-091262

(51) Int. Cl.
*G01N 27/409* (2006.01)
*G01N 27/41* (2006.01)
(52) U.S. Cl. ........ 204/427; 204/424; 204/426; 204/428; 204/429
(58) Field of Classification Search .................. 204/424, 204/426, 427, 428, 429
See application file for complete search history.

(56) References Cited

U.S. PATENT DOCUMENTS

| | | | |
|---|---|---|---|
| 5,672,811 A | 9/1997 | Kato et al. | |
| 5,763,763 A * | 6/1998 | Kato et al. | 205/781 |
| 5,948,964 A * | 9/1999 | Kato | 73/23.31 |
| 5,976,335 A * | 11/1999 | Kato et al. | 204/425 |
| 6,045,673 A * | 4/2000 | Kato et al. | 204/425 |
| 6,071,393 A | 6/2000 | Oshima et al. | |
| 2002/0017461 A1* | 2/2002 | Kunimoto et al. | 204/424 |
| 2004/0069629 A1 | 4/2004 | Tanaka et al. | |
| 2004/0231985 A1* | 11/2004 | Kato et al. | 204/426 |
| 2005/0211554 A1* | 9/2005 | Kurachi et al. | 204/426 |
| 2008/0105545 A1* | 5/2008 | Nakagaki et al. | 204/424 |

FOREIGN PATENT DOCUMENTS

| | | |
|---|---|---|
| EP | 0 678 740 | 10/1995 |
| EP | 0 810 430 | 12/1997 |
| EP | 1 739 416 A2 | 1/2007 |
| JP | 08-271476 A1 | 10/1996 |
| JP | 2007-40987 | 2/2007 |

* cited by examiner

*Primary Examiner* — Bruce Bell
(74) *Attorney, Agent, or Firm* — Burr & Brown

(57) ABSTRACT

A sensor for specifying a concentration of a predetermined gas component in a measurement gas on the basis of a current flowing in an electrolyte by decomposition of the predetermined gas component, includes an internal space; a reference gas space; a pumping cell capable of pumping out oxygen in the internal space by applying a predetermined voltage between a first electrode and a second electrode; and a measuring cell including third and fourth electrodes and measuring a current flowing when a voltage is applied between the third electrode and the fourth electrode; wherein the first electrode is formed of porous cermet consisted of a noble metal and an oxygen ion conductive solid electrolyte, and the porosity of the first electrode is greater than or equal to 10% and less than or equal to 50%.

4 Claims, 2 Drawing Sheets

F I G . 2
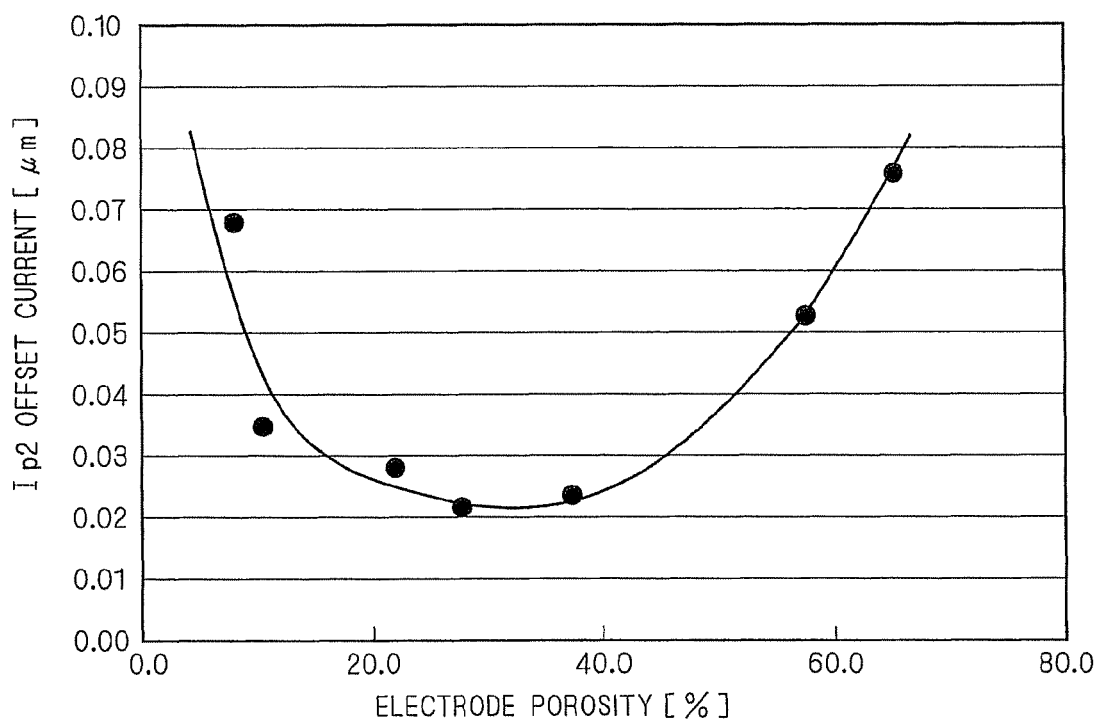

NOX SENSOR

BACKGROUND OF THE INVENTION

1. Field of the Invention

The present invention relates to a gas sensor composed of an oxygen ion conductive solid electrolyte, and specifically relates to a NOx sensor.

2. Description of the Background Art

Conventionally, various measuring devices have been used for determining a concentration of a desired gas component in a measurement gas. A known device of measuring a NOx concentration in a measurement gas such as a combustion gas, for example, is a NOx sensor formed of an oxygen ion conductive solid electrolyte, such as zirconia ($ZrO_2$) (see Japanese Patent Application Laid-Open No. 8-271476, for example).

According to a NOx sensor disclosed in Japanese Patent Application Laid-Open No. 8-271476, $O_2$ in a measurement gas introduced from outside is previously removed by pumping in the first internal space so as to make the measurement gas to be in a state of low oxygen partial pressure (a state in which oxygen partial pressure is lowered to the extent that the measurement of NOx is not affected by the presence of $O_2$ in the measurement gas), and thereafter, the measurement gas is introduced into the second internal space. Then, NOx is reduced in the measuring electrode by applying a constant voltage between the measuring electrode containing such as Pt and Rh provided in the second internal space and the reference electrode provided in the air. The NOx concentration is to be detected on the basis of a value of a current flowing at that time between the measuring electrode and the reference electrode, the value being proportional to the NOx concentration.

In order to improve the accuracy of measurement in a sensor for measuring the NOx concentration in the aforementioned manner, $O_2$ concentration in the second internal space is needed to be controlled accurately. To describe more in detail, when NOx does not exist in the measurement gas introduced into the second internal space, ideally, it is desirable that a current should not flow between the measuring electrode and the reference electrode. However, since $O_2$ actually exists even in a small amount of oxygen partial pressure, a current (offset current, zero-point current) induced by decomposition of $O_2$ flows when applying a voltage between the measuring electrode and the reference electrode. This offset current is to be superimposed on a current flowing when measuring the NOx concentration. Accordingly, the NOx concentration calculated in the aforementioned manner includes albeit only slightly an error attributed to this offset current. Therefore, the problem arises that the calculated NOx concentration is not necessarily accurate when the NOx concentration in the measurement gas is small.

SUMMARY OF THE INVENTION

The present invention relates to a gas sensor composed of an oxygen ion conductive solid electrolyte, and specifically relates to a NOx sensor.

According to the present invention, the NOx sensor in which a NOx concentration in a measurement gas is specified on the basis of a current flowing in a solid electrolyte by decomposition of NOx, includes: an internal space to which the measurement gas is introduced from an outside; a reference gas space to which a reference gas is introduced; a pumping cell including a first electrode and a second electrode, and pumping out oxygen in the internal space by applying a predetermined voltage between the first electrode and the second electrode; and a measuring cell including a third electrode and a fourth electrode, and measuring a current flowing between the third electrode and the fourth electrode when a voltage is applied between the third electrode and the fourth electrode; wherein the first electrode provided on a surface of the internal space, is formed of porous cermet consisted of a noble metal and an oxygen ion conductive solid electrolyte, and the porosity of the first electrode is greater than or equal to 10% and less than or equal to 50%; the second electrode is formed in a different space from the internal space; the third electrode is formed on the surface of the internal space, and the fourth electrode is formed in a different portion from the internal space.

According to the present invention, an error factor attributed to an $O_2$ gas in the measurement gas can be reduced, and in addition diffusion resistance of $O_2$ in an electrode is preferably reduced to suppress generation of a concentration gradient of $O_2$, allowing a NOx sensor having high accuracy of measurement.

It is therefore an object of the present invention to provide a NOx sensor having the accuracy of measurement which has been more improved than ever before.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a view for showing the relation of porosity and an offset current $Ip2_{ofs}$ in a sensor element when composing the sensor element with various porosity of an inside pump electrode 22 and an auxiliary pump electrode 51.

DETAILED DESCRIPTION OF THE INVENTION

<Gas Sensor>

Figure 1:
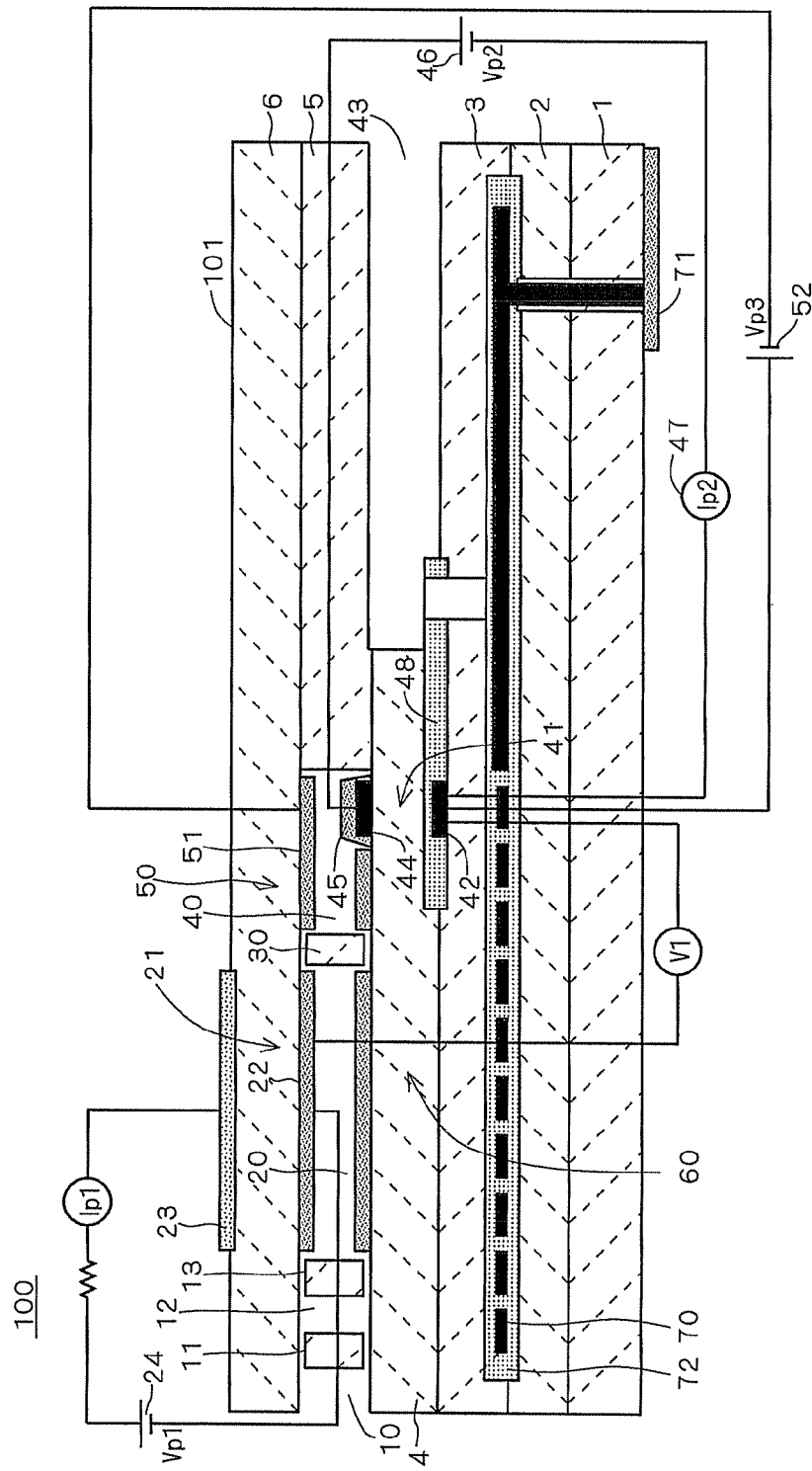
FIG. 1 is an outline sectional schematic view for showing a configuration of a gas sensor 100 according to a preferred embodiment of the invention.

FIG. 1 is an outline sectional schematic view for showing a configuration of a gas sensor 100 according to a preferred embodiment of the invention. The gas sensor 100 detects a predetermined gas component in a gas which is an object of measurement (a measurement gas), and further, measures a concentration thereof. The present embodiment will be described taking an example where the gas sensor 100 is a NOx sensor detecting nitrogen oxide (NOx) as an object component. The gas sensor 100 includes a sensor element 101 consisted of an oxygen ion conductive solid electrolyte such as zirconia ($ZrO_2$).

Specifically, the sensor element 101 includes a structure in which a first substrate layer 1, a second substrate layer 2, a third substrate layer 3, a first solid electrolyte layer 4, a spacer layer 5, and a second solid electrolyte layer 6 are integrally laminated in this order from a bottom seen in FIG. 1, each of the layers being consisted of an oxygen ion conductive solid electrolyte.

The sensor element 101 is manufactured by forming a laminated body consisted of green sheets including an oxygen ion conductive solid electrolyte such as zirconia as a ceramics component, then cutting and burning the laminated body. Roughly mentioned, the laminated body is formed by the following steps of; forming a penetrating portion on a plurality of green sheets, each of which corresponds to each layer of the sensor element, by punching or the like to form an internal space, printing a predetermined circuit pattern with a predetermined paste in accordance with a laminating position, and sequentially laminating these green sheets after printing and applying a bonding paste on each green sheet as an adhesive. A publicly known screen printing process is available for printing a pattern and an adhesive. Also, a publicly known drying process is available for a drying process after printing.

A gas inlet 10, a first diffusion control part 11, a buffer space 12, a second diffusion control part 13, a first internal space 20, a third diffusion control part 30 and a second internal space 40 are adjacently formed in this order to be in communication with one another between a lower surface of the second solid electrolyte layer 6 and an upper surface of the first solid electrolyte layer 4 at the end portion of the sensor element 101. The gas inlet 10, the buffer space 12, the first internal space 20 and the second internal space 40 are provided by hollowing out the spacer layer 5, which is an internal space with an upper portion sectioned by the lower surface of the second solid electrolyte layer 6, an lower portion sectioned by the upper surface of the first solid electrolyte layer 4, and a side portion sectioned by a side surface of the spacer layer 5. Each of the first diffusion control part 11, the second diffusion control part 13 and the third diffusion control part 30 is provided as two horizontally long slits (with an opening having a longitudinal direction in a direction perpendicular to Figure). A part from the gas inlet 10 to the second internal space 40 is also referred to as a gas distribution part.

A reference gas inlet space 43 is provided between an upper surface of the third substrate layer 3 and a lower surface of the spacer layer 5 at a position which is far from the end portion than the gas distribution part is. The reference gas inlet space 43 is an internal space with an upper portion sectioned by the lower surface of the spacer layer 5, a lower portion sectioned by the upper surface of the third substrate layer 3, and a side portion sectioned by a side surface of the first solid electrolyte layer 4. For example, air is introduced to the reference gas inlet space 43 as a reference gas.

The gas inlet 10 is open to an outside, and a measurement gas is brought into the sensor element 101 from the outside therethrough.

The first diffusion control part 11 provides a predetermined diffusion resistance to the measurement gas brought into from the gas inlet 10.

The buffer space 12 is provided in order to counteract concentration fluctuation of the measurement gas caused by pressure fluctuation (pulsation of exhaust pressure if a measurement gas is an emission gas of automobiles) of the measurement gas in the outside.

The second diffusion control part 13 provides a predetermined diffusion resistance to the measurement gas brought into the second diffusion control part 13 from the buffer space 12.

The first internal space 20 is provided as a space for controlling oxygen partial pressure in the measurement gas introduced through the second diffusion control part 13. The oxygen partial pressure is controlled by operating a main pumping cell 21.

The main pumping cell 21 is an electrochemical pumping cell composed of an inside pump electrode 22 provided on an almost whole surface in a part of the lower surface of the second solid electrolyte layer 6 facing the first internal space 20, an outside pump electrode 23 provided in a region corresponding to the inside pump electrode 22 on an upper surface of the second solid electrolyte layer 6 to be exposed to the outside, and a part of the second solid electrolyte layer 6 interposed between those electrodes. The inside pump electrode 22 and the outside pump electrode 23 are formed as porous cermet electrodes (e.g. porous electrodes consisted of cermet of noble metal such as Pt and Rh, and $ZrO_2$) which are oblong in a plane view. Further, the inside pump electrode 22 is formed using material in which reduction ability to an NO component in the measurement gas is weakened, or material without reduction ability. Details of the inside pump electrode 22 will be described later.

The main pumping cell 21 is provided with a variable power source 24 outside the sensor element 101. The variable power source 24 applies a desired pump voltage $Vp1$ between the inside pump electrode 22 and the outside pump electrode 23 to flow a pump current $Ip1$ in a positive direction or a negative direction between the inside pump electrode 22 and the outside pump electrode 23, allowing to pump out oxygen in the first internal space 20 to the outside or to pump in oxygen in the outside into the first internal space 20.

The third diffusion control part 30 provides a predetermined diffusion resistance to the measurement gas brought into the second internal space 40 from the first internal space 20.

The second internal space 40 is provided as a space for performing a process to measure concentration of nitrogen oxide (NOx) in the measurement gas introduced through the third diffusion control part 30.

A NOx concentration can be measured by operating a measuring pumping cell 41. The measuring pumping cell 41 is an electrochemical pumping cell composed of a reference electrode 42 interposed between the upper surface of the third substrate layer 3 and the first solid electrolyte layer 4, a measuring electrode 44 provided on the upper surface of the first solid electrolyte layer 4 facing the second internal space 40, spaced apart from the third diffusion control part 30, and the first solid electrolyte layer 4. Each of the reference electrode 42 and the measuring electrode 44 is a porous cermet electrode which is substantially oblong in a plane view. The reference electrode 42 is surrounded by an air induction layer 48 consisted of porous alumina and leading to a reference gas introduction space. The measuring electrode 44 is composed of porous cermet of metal resolving NOx which is a measurement gas component, and zirconia. Therefore, the measuring electrode 44 also serves as a NOx reduction catalyst for resolving NOx in the atmosphere of the second internal space 40.

Moreover, the measuring electrode 44 is covered with a fourth diffusion control part 45. The fourth diffusion control part 45 is a film consisted of alumina, and functions to limit the amount of NOx flowing into the measuring electrode 44.

The measuring pumping cell 41 is provided with a DC power source 46 applying a pump voltage $Vp2$ which is a fixed voltage between the measuring electrode 44 and the reference electrode 42 to resolve NOx. Thereby, oxygen is generated in the atmosphere of the second internal space 40, and then the oxygen is pumped out to the reference gas inlet space 43. A pump current $Ip2$ allowed to flow by the operation of the measuring pumping cell 41 is detected by an ammeter 47. The gas sensor 100 calculates the NOx concentration by using the pump current $Ip2$ being substantially proportional to the concentration of NOx existing in the measurement gas in a state in which oxygen partial pressure is maintained constant in the second internal space 40.

Oxygen partial pressure is previously controlled in the first internal space 20, and thereafter, oxygen partial pressure in the measurement gas introduced through the third diffusion control part 30 is further controlled in the second internal space 40 by an auxiliary pumping cell 50. Accordingly, the gas sensor 100 can perform the measurement of a NOx concentration with the high accuracy.

The auxiliary pumping cell 50 is an auxiliary electrochemical pumping cell composed of an auxiliary pump electrode 51 provided on a substantially whole surface in a part of the lower surface of the second solid electrolyte layer 6 facing the second internal space 40, the second solid electrolyte layer 6, the spacer layer 5, the first solid electrolyte layer 4 and the reference electrode 42.

Similarly to the inside pump electrode 22, the auxiliary pump electrode 51 is formed using material in which reduction ability to an NO component in the measurement gas is weakened, or material without reduction ability. Details of the auxiliary pump electrode 51 will be described later.

The auxiliary pumping cell 50 is provided with a DC power source 52 outside the sensor element 101. The DC power source 52 applies a fixed voltage Vp3 between the auxiliary pump electrode 51 and the reference electrode 42 to pump out oxygen in the atmosphere of the second internal space 40 into the reference gas inlet space 43.

Moreover, the sensor element 101 includes an oxygen partial pressure detecting sensor cell 60 which is an electrochemical pumping cell composed of the inside pump electrode 22, the reference electrode 42, the second solid electrolyte layer 6, the spacer layer 5 and the first solid electrolyte layer 4.

The oxygen partial pressure detecting sensor cell 60 detects oxygen partial pressure in the atmosphere of the first internal space 20 on the basis of an electromotive force V1 generated between the inside pump electrode 22 and the reference electrode 42 which is caused by the difference of oxygen concentration between the atmosphere of the first internal space 20 and a reference gas (air) of the reference gas inlet space 43. The detected oxygen partial pressure is used for feedback controlling the variable power source 24. Specifically, a pump voltage applied to the main pumping cell 21 is controlled so as to set oxygen partial pressure in the atmosphere of the first internal space 20 at a predetermined value which is lower enough to be able to control oxygen partial pressure in the second internal space 40.

The sensor element 101 includes a heater 70 formed to be interposed between the second substrate layer 2 and the third substrate layer 3 from above and below. The heater 70 generates heat by power feeding from outside through a heater electrode 71 provided on a lower surface of the first substrate layer 1. Heat generation by the heater 70 allows to enhance oxygen ion conductivity of solid electrolyte composing the sensor element 101. The heater 70 is buried over the whole area from the first internal space 20 to the second internal space 40 so that a predetermined area of the sensor element 101 is heated and kept warm at a predetermined temperature. A heater insulating layer 72 consisted of alumina or the like is formed on an upper surface and a lower surface of the heater 70 in order to obtain electronic insulation between the second substrate layer 2 and the third substrate layer 3 (hereinafter, the heater 70, the heater electrode 71 and the heater insulating layer 72 are also collectively referred to as a heater part).

In the gas sensor 100 having the above-described structure, the measurement gas is provided with the measuring pumping cell 41, with oxygen partial pressure constantly maintained at a fixed low value (a value substantially not affecting the measurement of NOx) by operating the main pumping cell 21 and the auxiliary pumping cell 50. Accordingly, a pump current is to be substantially proportional to the reduced NOx concentration, the pump current flowing in the measuring pumping cell 41 by pumping out oxygen generated by a reduction of NOx.

<Reduction of Offset Current>

As described above, the gas sensor 100 calculates the NOx concentration by using the pump current Ip2 being substantially proportional to the NOx concentration existing in the measurement gas in a state in which oxygen partial pressure is maintained constant in the second internal space 40. An offset current $Ip2_{ofs}$ flowing due to decomposition of $O_2$ existing in a small amount in the measurement gas is superimposed on the pump current Ip2. The offset current $Ip2_{ofs}$ corresponds to a current flowing when the NOx concentration is zero (when NOx does not exist in the measurement gas). Thus, as the value of the offset current $Ip2_{ofs}$ is small, it can be said that the gas sensor 100 has more preferable accuracy of measurement.

FIG. 2 shows the relation of the porosity and the offset current $Ip2_{ofs}$ about the sensor elements 101. These sensor elements 101 have been composed varying porosity (also referred to as an electrode porosity) of the inside pump electrode 22 and the auxiliary pump electrode 51 which are provided at an internal-space-side of the main pumping cell 21 and the auxiliary pumping cell 50, for pumping out oxygen from inside the sensor element 101. The weight ratio of a noble metal component and zirconia is set to be 6:4. In the present embodiment, the porosity is defined as a ratio of a volume of an air gap in the actual electrode to the whole volume of the electrode in the case of supposing that the electrode is completely tight with no space.

As shown in FIG. 2, the porosity of the inside pump electrode 22 and the auxiliary pump electrode 51 correlates with the offset current $Ip2_{ofs}$. When the porosity is around 30% to 40%, the offset current $Ip2_{ofs}$ is minimum. The inventors of the present invention have found such observation for the first time.

In the case where the electrode porosity is less than or equal to 10%, diffusion resistance of $O_2$ becomes large in diffusing from the surface side of both electrodes to a layer composed of an oxygen ion conductive solid electrolyte through the air gap ($O_2$ is difficult to diffuse). Therefore, the problem arises that oxygen partial pressure in the surfaces of both electrodes (i.e., oxygen partial pressure in the first and second internal space) is too high with respect to the targeted oxygen partial pressure (concentration electromotive force), in other words, the actual oxygen partial pressure is not lowered as the targeted oxygen partial pressure. In this case, a concentration gradient of $O_2$ in which a concentration of $O_2$ is high at the surface side and becomes lower towards inside is remarkably created to promote generation of oxygen ion by decomposition of $H_2O$ and $CO_2$ in the measurement gas, causing the problem that the accuracy of measurement of the NOx concentration may be deteriorated.

In contrast, when the electrode porosity is greater than or equal to 50%, the number of conduction paths in the electrodes decreases so that conductive resistance of oxygen ion generated by decomposition of $O_2$ in the both electrodes becomes too high. The defects have been confirmed to be caused as a result that the main pumping cell 21 and the auxiliary pumping cell 50 cannot function enough to pump out oxygen from the first and second internal space to obtain the targeted oxygen partial pressure.

In view of the above, in the sensor element 101 according to the present embodiment, the inside pump electrode 22 and the auxiliary pump electrode 51 are formed to have the porosity greater than or equal to 10% and less than or equal to 50%. Thus, even if some fluctuation is generated in the offset current $Ip2_{ofs}$, the NOx concentration can be accurately measured substantially without having any problems. For instance, the offset current $Ip2_{ofs}$ in the above case is very small with such a value of less than or equal to 5% of the pump current Ip2 flowing to correspond to NOx having a concentration of 500 ppm. Thus, even NOx having much lower concentration can be measured with an error by several percentages. In view of the result shown in FIG. 2, it is preferable that the electrode porosity should be set greater than or equal to 15% and less than or equal to 40% from the standpoint of reducing the offset current $Ip2_{ofs}$ as much as possible.

Diffusion resistance of $O_2$ in the electrodes can be preferably reduced, and generation of the concentration gradient of $O_2$ can be preferably suppressed by setting the porosity within the above range.

There are various methods to form the inside pump electrode 22 and the auxiliary pump electrode 51 which are porous cermet electrodes to have the porosity within the aforementioned range. For instance, when the electrode is formed with the aforementioned screen printing technology, it is preferable to form an electrode pattern of the inside pump electrode 22 and the auxiliary pump electrode 51 with a conductive paste made by appropriately controlling a configuration, a particle diameter, a specific surface and the like of raw powder of a noble metal component and $ZrO_2$ to be material for the cermet electrode, or with a conductive paste made by further mixing a sublimation pore-forming agent and the above raw powder. For the latter case, the porosity can be set 30% when the additive amount of the pore-forming agent is 20 vol %, and the porosity can be set 35% when the additive amount is 40 vol %.

As described above, according to the present embodiment, the gas sensor with high accuracy of measurement can be obtained, in which the error factor attributed to $O_2$ gas in the measurement gas can be reduced and the diffusion resistance of $O_2$ in the electrode can be preferably lowered by setting the porosity of the electrode provided at a side of the internal space of a pumping cell for pumping out oxygen from the inside of the sensor element of the gas sensor within a predetermined range, suppressing generation of a concentration gradient of $O_2$.

<Variation>

The porosity of the inside pump electrode 22 is not necessarily same as the porosity of the auxiliary pump electrode 51, but may be different within the range determined as described above.

The preferred embodiment to set the value of the electrode porosity within the aforementioned range is not limited to the gas sensor including two internal spaces as described above, but applicable to a gas sensor including only one internal space. It is further generally applicable to a gas sensor for measuring a current derived from oxygen ion generated by decomposition of $O_2$ or oxide gas, using an oxygen ion conductive solid electrolyte.

The placement position of each electrode is not limited to the above preferred embodiment, but may employ the other placement pattern, as long as ensuring the function of each cell.

Furthermore, in the above preferred embodiment, the measuring pumping cell 41 is formed between the measuring electrode 44 and the reference electrode 42, and the auxiliary pumping cell 41 is formed between the auxiliary pump electrode 51 and the reference electrode 42. Instead, the measuring pumping cell 41 may be formed between the measuring electrode 44 and the outside pump electrode 23, and the auxiliary pumping cell 41 may be formed between the auxiliary pump electrode 51 and the outside pump electrode 23.

While the invention has been shown and described in detail, the foregoing description is in all aspects illustrative and not restrictive. It is therefore understood that numerous modifications and variations can be devised without departing from the scope of the invention.

What is claimed is:

1. A NOx sensor composed of an oxygen ion conductive solid electrolyte, in which a NOx concentration in a measurement gas is specified on the basis of a current flowing in said solid electrolyte by decomposition of NOx, said NOx sensor comprising:
    an internal space to which the measurement gas is introduced from an outside;
    a reference gas space to which a reference gas is introduced;
    a pumping cell including a first electrode and a second electrode and pumping out oxygen in said internal space by applying a predetermined voltage between said first electrode and said second electrode; and
    a measuring cell including a third electrode and a fourth electrode and measuring a current flowing between said third electrode and said fourth electrode when a voltage is applied between said third electrode and said fourth electrode; wherein
    said first electrode provided on a surface of said internal space is formed of porous cermet consisting of a noble metal and an oxygen ion conductive solid electrolyte using a material in which a reduction ability for an NO component in the measurement gas is weakened or a material without a reduction ability, and the porosity of said first electrode is greater than or equal to 30% and less than or equal to 40%;
    said second electrode is formed in a different space from said internal space;
    said third electrode, which is composed of a porous cermet of a metal for resolving NOx and zirconia, is formed on the surface of said internal space, and said fourth electrode is formed in a different portion from said internal space.

2. The NOx sensor according to claim 1, wherein
said internal space includes:
    a first internal space to which said measurement gas is introduced from said outside, and
    a second internal space formed to be in communication with said first internal space under a predetermined diffusion resistance,
said pumping cell includes:
    a main pumping cell including said first electrode in said first internal space, and
    an auxiliary pumping cell including said first electrode in said second internal space,
said third electrode is formed in said second internal space, and
said second electrode is formed to be shared by said main pumping cell and said auxiliary pumping cell.

3. The NOx sensor according to claim 2, further comprising an oxygen partial pressure detection cell for detecting an oxygen partial pressure in an atmosphere of said first internal space, said oxygen partial pressure detecting cell sharing said first electrode with said main pumping cell and sharing said fourth electrode with said measuring cell and said auxiliary pumping cell, wherein
    said oxygen partial pressure detecting cell detects oxygen partial pressure in the atmosphere of said first internal space on the basis of an electromotive force generated between said first electrode and said fourth electrode which is caused by the difference of oxygen concentration between the atmosphere of said first internal space and the reference gas of said inlet space.

4. The NOx sensor according to claim 2, wherein said second electrode also functions as said fourth electrode.

* * * * *